United States Patent
Kirnasovsky et al.

(10) Patent No.: US 8,650,017 B2
(45) Date of Patent: Feb. 11, 2014

(54) SYSTEM AND METHOD OF EVALUATION OF STOCHASTIC INTERACTIONS OF A SOLUBLE LIGAND WITH A TARGET CELL POPULATION FOR OPTIMIZATION OF DRUG DESIGN AND DELIVERY

(75) Inventors: Oleg U. Kirnasovsky, Bene Ataroth (IL); Vladimir Vainstein, Bene Ataroth (IL); Yuri Kogan, Bene Ataroth (IL); Zvia Agur, Ramat Gan (IL)

(73) Assignee: Optimata Ltd., Ramat Gan (IL)

( * ) Notice: Subject to any disclaimer, the term of this patent is extended or adjusted under 35 U.S.C. 154(b) by 838 days.

(21) Appl. No.: 11/449,648

(22) Filed: Jun. 9, 2006

(65) Prior Publication Data

US 2007/0054331 A1 Mar. 8, 2007

Related U.S. Application Data

(60) Provisional application No. 60/689,542, filed on Jun. 13, 2005.

(51) Int. Cl.
*G06G 7/48* (2006.01)
*G06G 7/58* (2006.01)
*G01N 33/48* (2006.01)
*G01N 31/00* (2006.01)

(52) U.S. Cl.
USPC .................. 703/11; 703/12; 702/19; 702/22

(58) Field of Classification Search
None
See application file for complete search history.

(56) References Cited

U.S. PATENT DOCUMENTS 5,699,268 A * 12/1997 Schmidt ........................ 702/27
2002/0095258 A1 * 7/2002 Agur et al. .................... 702/19

OTHER PUBLICATIONS

Friedrich, et al. Antibody-Directed Effector Cell Therapy of Tumors: Analysis and Optimization Using a Physiologically Based Phamacokinetic Model, Neoplasia, 2002, 4(5), 449-463.*
Renner et al., Cure of Xenografted Human Tumors by Bispecific Monoclonal Antibodies and Human T Cells, Science, 1994, 264, 833-835.*
Hlavacek et al. (Mathematical Biosciences, 2002, 176, 185-202).*
Sun et al. (Journal of Pharmaceutical Sciences, 87(6) 732-737).*
Rutledge et al. (Proceedings of the Annual Symposium on Computer Application in Medical Care, 1989, Nov. 8, 315-319).*
Lennert et al. (Proceedings of the Annual Symposium on Computer Application in Medical Care, 1988, Nov. 8, 308-312).*
Resat et al. (Biophysical Journal, 2003, 85, 730-743).*
Sun et al. (Journal of Pharmaceutical Sciences, 1998, 87(6) 732-737).*
TL Jackson et al.; Mathematical and experimental analysis of localization of anti-tumour antibody-enzyme conjugates.; British Journal of Cancer, 1999, 80(11), 1747-1753.

(Continued)

Primary Examiner — Larry D Riggs, II
(74) Attorney, Agent, or Firm — Sughrue Mion, PLLC

(57) ABSTRACT

A computer system for recommending an optimal treatment protocol comprising a model of biological processes related to a disease. A treatment protocol generator generates a plurality of treatment protocols for treating a disease using drugs. A selector selects an optimal treatment protocol from the plurality of treatment protocols based on model. The model further comprises a pharmacokinetics macro module adapted to analyze interactions between a ligand and a population of target cells at a tissue level. The model further comprises a pharmacokinetics micro module adapted to analyze interactions between the ligand and a cell at an individual cell level. The pharmacokinetics micro module is adapted to model behavior of the ligand and receptors related to single cell level of ligand-cell interactions, as a stochastic process.

32 Claims, 3 Drawing Sheets

(56) References Cited

OTHER PUBLICATIONS

Slomorovski, K. et al.; New TPO treatment schedules of increased safety and efficacy: pre-clinical validation of a thrombopoiesis simulation model,; British Journal of Haematol, 123, 2003, pp. 683-691.

Baxter, L.T. et al.; Physiologically based pharmacokinetic model for specific and nonspecific monoclonal antibodies and fragments in normal tissues and human tumor xenografts in nude mice.; Cancer Research 54, Mar. 15, 1994, pp. 1517-1528.

C. Penna et al., Antitumor x Anti-CD3 Bifunctional Antibodies Redirect T-Cells Activated in Vivo with *Staphylococcal* Enterotoxin B to Neutralize Pulmonary Metastases. Cancer Research, May 15, 1994, ; pp. 2738-2743; vol. 54.

William E. Boyce et al., "Elementary Differential Equations and Boundary Value Problems", John Wiley & Sons, Inc., New York, 2005, 8$^{th}$ Edition.

M. Ainsworth et al., "Theory and Numerics of Ordinary and Partial Differential Equations", Oxford University Press, Oxford, 1995, Advances in Numerical Analysis, vol. 4.

William Feller, An Introduction to Probability Theory and Its Applications, John Wiley & Sons, Inc., New York, 1966, 1971, vol. 2, 2$^{nd}$ Edition.

\* cited by examiner

SYSTEM AND METHOD OF EVALUATION OF STOCHASTIC INTERACTIONS OF A SOLUBLE LIGAND WITH A TARGET CELL POPULATION FOR OPTIMIZATION OF DRUG DESIGN AND DELIVERY

CROSS REFERENCE TO RELATED APPLICATIONS

This application claims priority from U.S. provisional application No. 60/689,542 filed on Jun. 13, 2005.

REFERENCES

The following documents provide useful background information, for which, they are incorporated herein by reference.

Jackson, T. L. et al. (1999) Mathematical and experimental analysis of localization of anti-tumor antibody-enzyme conjugates. Br. J. Cancer 80:1747-1753.

Friedrich, S. W. et al. (2002) Antibody-directed effector cell therapy of tumors: analysis and optimization using a physiologically based pharmacokinetic model. Neoplasia 4:449-463.

Baxter, L. T. et al. (1994) Physiologically based pharmacokinetic model for specific and nonspecific monoclonal antibodies and fragments in normal tissues and human tumor xenografts in nude mice. Cancer Res. 54:1517-1528.

Skomorovski, K. et al. (2003) New TPO treatment schedules of increased safety and efficacy: pre-clinical validation of a thrombopoiesis simulation model. Br. J. Haematol. 123: 683-91.

Boyce, W. E. and DiPrima, R. C., Elementary differential equations and boundary value problems, Wiley, N.Y., 2004.

Ainsworth M., Levesley J., Light W. A. and Marletta M. (eds.) Theory and numerics of ordinary and partial differential equations, Oxford University Press, NY, 1995.

Feller, William. An Introduction to Probability Theory and Its Applications, Wiley, NY 1968, 1971. 2 Vols., Second Edition.

TECHNICAL FIELD

The disclosed teachings relate generally to prediction of interactions of a soluble ligand (a drug) with a target cell population. The disclosed teachings are embodied in systems, methods and computer program products for predicting the progression of a biological system, and for prediction and optimization of treatment of a disease. These systems, methods and computer program products can be implemented for physiologically based design of new drugs and optimization and individualization of their delivery to the patients.

BACKGROUND

During last two decades the progress in the molecular biology has led to development of "the targeted molecular therapy", which consists of macromolecular drugs that specifically interact with a certain target cell population. This interaction is frequently mediated by a specific binding of a ligand (here and further on—any soluble substance used as a part of treatment for certain disease, e.g. drug, prodrug, etc.) to a receptor that is expressed on the cell surface (here and further on we use the term "receptor" in a broad sense—any macromolecule expressed on the cell surface, which specifically binds the mentioned ligand).

Pharmacokinetics (PK) and pharmacodynamics (PD) of ligands (both unconjugated ones and their conjugates with chemotherapeutic, enzymatic, radioactive and other agents) are complex and include PK in the blood, the perfusion—and diffusion—limited transport phenomena in the blood-tissue border, binding of ligands to their receptors, and finally their effect on the target cells (cell-mediated ligand-dependent cytotoxicity, a complement activation, an effect induced by the conjugate, a cell signaling cascade induction by an activation of the receptor upon ligand binding, etc). This complexity demands development of computational tools for optimization of drug design, treatment protocol choice and individualization of the treatment.

Several aspects of this complex process (including the perfusion, the diffusion, the tissue distribution, the conjugate efficacy) have been analyzed in the case of monoclonal antibodies by mathematical models (Jackson et al., Friedrich et al., Baxter et al.). This analysis can be very important for an evaluation of applicability of a specific monoclonal antibody (with or without a conjugate) to a certain disease prior to performing time—and resource—consuming clinical trials. However, in all cited models, description of the process of binding of a ligand (a monoclonal antibody) to their target is based solely on two values—the average number of receptors (antigens) per cell and the dissociation constant (the ratio of dissociation and the association rates between a specific monoclonal antibody and its antigen). These models do not take into account the fact that binding and dissociation of a ligand are stochastic processes, and consequently, the number of the bound antibodies can vary considerably between individual cells even if they are identical with respect to the antigen kinetics. Therefore drug efficacy can be easily over- or underestimated, rendering exact quantitative predictions of the in vivo effect highly unreliable.

SUMMARY

The disclosed teachings are aimed at overcoming some of the above noted problems. The disclosed teachings specifically provide analysis of interaction of a soluble ligand with population(s) of target cells. The disclosed techniques are very general, since they are based on a small number of biologically justified assumptions. The techniques can be implemented for different types of normal and pathological cell populations and various ligand-receptor pairs.

To realize the advantages there is provided a computer system for recommending an optimal treatment protocol comprising a model of biological processes related to a disease; a treatment protocol generator for generating a plurality of treatment protocols for treating a disease using drugs; and a selector adapted to select an optimal treatment protocol from said plurality of treatment protocols based on the model. The model further comprises a pharmacokinetics macro module adapted to analyze interactions between a ligand and a population of target cells at a tissue level. The model further comprises a pharmacokinetics micro module adapted to analyze interactions between the ligand and a cell at an individual cell level. The pharmacokinetics micro module is adapted to model behavior of the ligand and receptors related to single cell level of ligand-cell interactions, as a stochastic process.

In another specific enhancement, the model further comprises a pharmacodynamics module that is adapted to model actual effects of ligands on the population of target cells using pharmacokinetics modules' outcome.

More specifically, the pharmacokinetics micro module is operable to compute a distribution of cells according to a number of bound receptors and a number of free receptors in a cell.

More specifically, the distribution of cells is provided to the pharmacodynamics module.

In another specific enhancement, the stochastic process is a Markov chain.

In another specific enhancement the ligand is a monoclonal antibody.

In another specific enhancement, the receptor is an antigen on the cell surface of said target cells.

In another specific enhancement, the target cell population is cancerous.

In another specific enhancement, the pharmacokinetics macro module is a system of differential equations, each of said differential equation describing behavior of a separate parameter.

More specifically, the Markov chain is countable and continuous in time.

More specifically, the differential equations include at least one selected from an equation denoting molar concentrations of free antibodies as a function of time, equation denoting molar concentrations of free antigens as a function of time, equation denoting molar concentrations of bound antigens as a function of time, equation denoting molar concentrations of internalized conjugates.

More specifically, a base set of the Markov chain is chosen to form an infinite grid of states wherein each of said states is a cell that includes a set of free antigens and a set of bound antigens.

More specifically, the model is adapted to consider at least one of the next moves selected from: a free antigen binding with an antibody; a free antigen undergoing internalizations, a bound antigen undergoing internalization, a bound antigen disassociating and a new free antigen being produced. Each of the next moves proceeds with a predetermined probability density.

In another specific enhancement, the pharmacokinetics macro module is assumed to arrive at steady state prior to implementing the micro module.

In another specific enhancement, the pharmacodynamics module includes an effector function that computes ligand effects.

In another specific enhancement, the system further comprises a model modifier operable to modify the model based on parameters specific to an individual.

Another aspect of the disclosed teachings is a computer-implemented method for recommending an optimal treatment protocol for treating a disease comprising modeling biological processes related to the disease. A plurality of treatment protocols are enumerated for treating the disease using drugs. An optimal treatment protocol is selected from said plurality of treatment protocols based on the modeling. The optimal treatment is recommended to the patient. The modeling further includes analyzing interactions between a ligand and a population of target cells at a tissue level using a pharmacokinetics macro module. The modeling further includes analyzing interactions between the ligand and a cell at an individual cell level using a pharmacokinetics micro module. The pharmacokinetics micro module models behavior of the ligand and receptors related to single cell level of ligand-cell interactions, as a stochastic process.

BRIEF DESCRIPTION OF THE DRAWINGS

The disclosed teachings will become more apparent by describing in detail examples and embodiments thereof with reference to the attached drawings in which.

DETAILED DESCRIPTION

Figure 1:
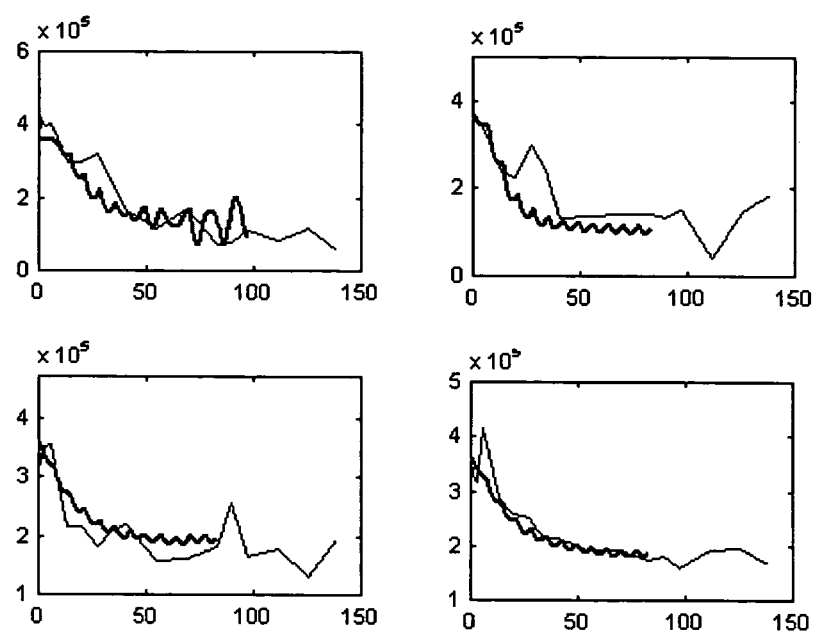
FIG. 1 shows drug-induced thrombocytopenia in healthy Cynomolgus monkeys during a weekly administration of a drug (a monoclonal antibody). The experimental results (the thinner lines) and the predictions of mathematical model (the thicker lines) of 4 different monkeys are presented. x-axis is in days, y-axis is in cell counts per ml.
Figure 2:
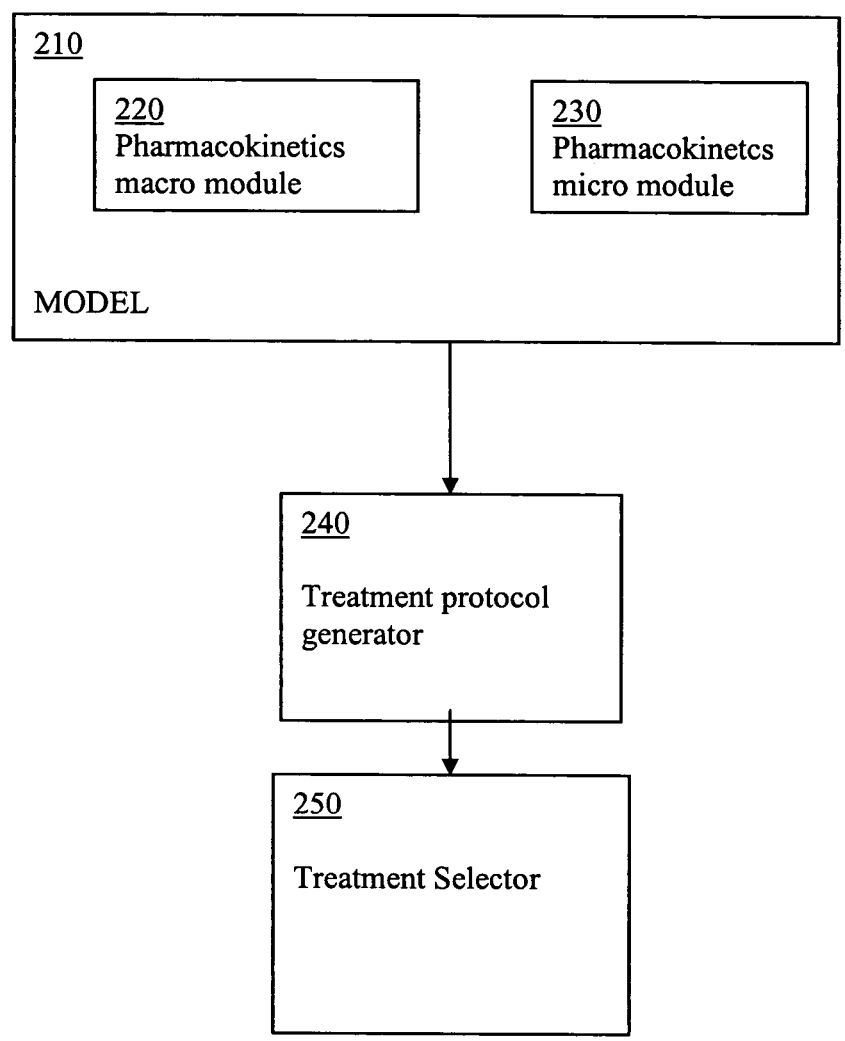
FIG. 2 shows an exemplary block diagram depicting the overall system.
Figure 3:
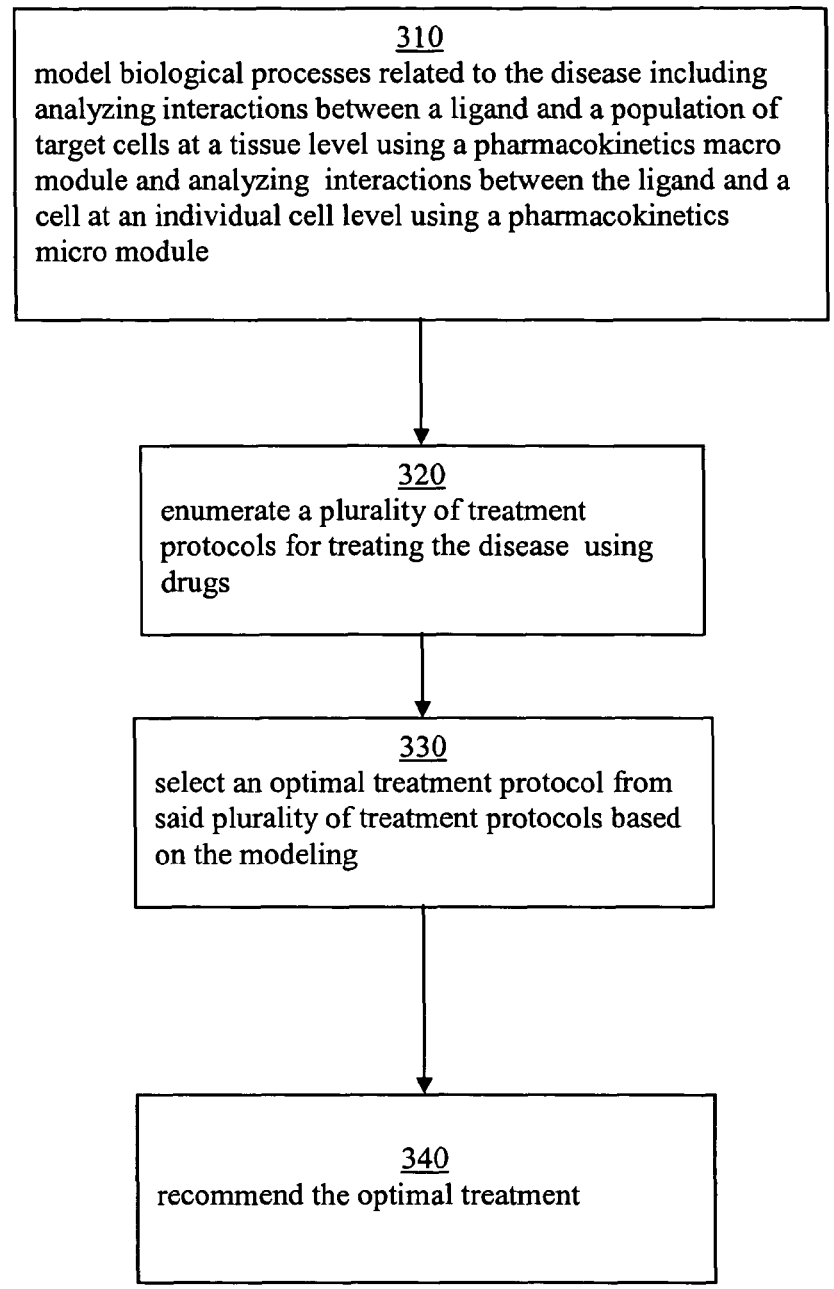
FIG. 3 shows an exemplary flowchart illustrating the methodology of the disclosed teachings.

Systems and methods have been disclosed for identifying optimal treatment strategies for a general patient and a specific individual patient, and for predicting progression of a biological process and treatment, using selected parameters. The techniques are based on biological and clinical knowledge, mathematical models, computer simulations, and optimization methods.

Initially, a model 210 is created. This includes modules to simulate all the relevant biological, clinical and pharmaceutical processes. These modules include mathematical models for processes that affect interaction of a soluble ligand with the receptor-bearing target cell population(s). Examples of these processes include interactions involving pharmacokinetics (PK), pharmacodynamics (PD), cytotoxic and cytostatics, or any other method of affecting cell biology and/or causing cell death, with associated biological processes. The biological processes are modeled in step 310.

The combination of these models provides a detailed mathematical model of the overall bio-clinical scenario in a general sense or for a specific patient, together with the specific effects of a particular treatment. Once the comprehensive model is constructed, the characteristic parameters are incorporated in it. The characteristic parameters could be either population averaged or patient specific. In the general model, average patient parameters are incorporated. The average patient parameters include parameters related to biological process dynamics, average drug PK and average drug PD.

Then a protocol space is generated using a protocol generator 240 in step 320. To do this, possible values of certain parameters such as drug doses, dosing intervals, etc. are considered. Thus, a number of possible treatment protocols are generated in step 320. This number could be very large because of the number of possible values. The amount of possibilities depends on the number of parameters considered and their values' ranges.

A fitness function is then constructed by mathematically considering different possible factors, which may be influenced by the treatment. These may include target cell population load, cytotoxicity to normal or diseased tissues, other side effects, cost of treatment, etc.

The user can alter certain specific parameters in the fitness function so as to adjust this function to the user's specific goals. The user can be anybody, including a medical doctor, a scientist or a drug developer. Based on the selected parameters, the fitness function is applied. This results in the calculation of a fitness score for each and every protocol in the protocol space. Finally, the optimization step is carried out in the treatment selector 250, either by search heuristics or by analytical methods, in order to select the optimal treatment protocol in step 330 from all the scored possibilities. The analytical methods include the use of Operations Research techniques. In selecting the optimal treatment protocol cytotoxic effects as well as treatment efficacy are incorporated, as well as other objectives of the said fitness function. The heuristics, or rules of thumb employed include computational facility. The optimal treatment protocol is a combination of disease and treatment strategy, including type of treatment, device, drug or drug combination, radiotherapy, surgery and treatment schedule. The optimal protocol is recommended to the patient in step 340.

In this way, a disease specific, patient specific, situation specific, treatment type specific, drug specific, or an objective specific treatment protocol may be obtained. The actual time it takes once the parameters are entered may be negligibly short or up to hours, depending on the length of the simulated treatment period and the power of the specific search heuristics and the computational tools, making this a very feasible tool.

Systems and methods embodying the above disclosed technique for a general patient as well as for an individual patient are within the scope of the present invention.

General Exemplary Implementation

A general exemplary implementation is described herein. The exemplary system consists of three modules: the PK module, which describes the processes of ligand interaction with its receptor on the target cells, the PD module, which describes the actual effect of the ligand on the target cell population, and the treatment optimization module (TO), which computes the optimal treatment schedule for the given biological system.

1. PK Module Description

An embodiment of the present invention involves the disclosed techniques for modeling the interactions of a ligand with a target cell population.

First, the verbal model of ligand/target-tissue/target-cell interactions is constructed for a specific combination of a ligand and a target cell population, based on the available state of the art biological information:

a) Ligand PK in the blood is described. This includes ligand administration schedule (per os, intravenous, subcutaneous, etc.); ligand distribution in the patient's body; ligand metabolism and elimination by different organs (liver, kidneys, etc.).

b) Ligand transport into the target tissue is described. This description takes into account tissue perfusion by the blood, transition of the blood-tissue barrier by the drug, and drug diffusion in the tissue.

c) Ligand stochastic interaction with receptor-bearing cell population is described. This includes binding, dissociation and non-specific elimination of the ligand; receptor production; and internalization of bound and free receptors. The interaction of a ligand with its receptor can be of a different stoichiometry—one ligand molecule binds several receptors, or several ligand molecules bind one receptor, etc. A bi- (multi-) valent ligand can also induce its effect through binding to two (or more) different receptors, which are present on different target cell populations (for example, a bivalent ligand that binds both cancer cells and cytotoxic lymphocytes). These specific cases, as well as many other possibilities, constitute examples of the presented general model of a soluble ligand interaction with target cell population(s). In each such case target cell distribution is modified accordingly (in addition to free, bound and internalized receptors there can be mono- and multi-bound receptors, ligands bound to both target and effector cells, etc.).

The disclosed teachings include a unique and novel combination of the above three steps.

Upon construction of the case-specific verbal model it is translated into a mathematical model. This model is described on two scales—tissue scale (pharmacokinetics macro module 220) and individual cell scale (pharmacokinetics micro module 230).

The macro-scale is modeled as a system of differential equations. Each equation describes dynamics of the behavior of one system variable (such as ligand concentration in the blood, number of target cells, total number of free and bound receptors, etc.) and its dependence on the system parameters as well as other variables. All the calculations are repeated at each time step of ligand administration and coupled with intrinsic dynamics of the target cell population (cell division, cell movement etc.).

Analysis of the steady state of the system of differential equations and its stability is then performed, using analytical (for examples of analytical techniques see Boyce and DiPrima) and/or numerical methods (for examples of numerical methods see Ainsworth M. et al.).

Furthermore, for this exemplary implementation, the stochastic nature of the ligand-cell interactions on the microscale is analyzed using Markov chain theory (see Feller for a general description of stochastic methods and Markov chain theory).

A Markov chain which continuous in time is constructed. Such a Markov chain describes all the processes aforementioned in item c) on the individual cell level.

If macro-scale processes (such as blood PK of the ligand, cell proliferation and death, etc.) are slow enough in comparison with micro-scale processes (ligand binding and dissociation, etc.), "quasi-steady state" assumption is made, and quasi-steady state values of the general variables (resultant from the differential equations analysis) are incorporated in the Markov chain analysis.

Otherwise, numerical methods are applied to the whole two-scale system, which is implemented in a computer program that simulates its behavior. Calculation of the dynamics of distribution of the target cell population with respect to the numbers of all types of receptors (such as free, internalized, bound, multi-bound, etc.) is performed. This distribution and its dynamics in time constitute the final output of the PK module and the input into the PD module.

2. PD Module Description

As has been indicated previously, PD describes the actual effects of the ligand on the target cells. The method of analysis of the PD effects consists of several steps.

I. Construction of the effector function (EF), which computes the ligand effect (such as cell death, proliferation inhibition, etc.) based on the number of "effective ligands" on a cell (in each specific case effective ligands can be bound ligands, internalized ligands, multi-bound ligands, etc.). The form of EF depends critically on the type of ligand-induced effects. The examples of such effects can be found in subsequent sections.

Due to its flexibility, the disclosed techniques allow for an incorporation of different forms of EF. This includes (but is not limited to) binding competition of a ligand with the natural receptor ligand; direct cytotoxicity of bound, multi-bound or internalized ligand; complement-mediated cytotoxicity; cell-mediated cytotoxicity; local activation of a prodrug by a ligand-bound enzyme; cytotoxicity induced by a ligand-bound radionuclide, PD mechanisms that depend on the whole history of ligand-receptor interactions, etc.

II. Coupling of EF to the target cell distributions calculated in the PK module. This step allows for calculation of the total effect of the ligand on the target cell population at each time step of its administration according to the following formula:

$$D = \sum_{i=0}^{\infty} W_i B(i).$$

Here $W_i$ is a number of cells with i "effective receptors", $B(i)$ is the corresponding value of EF in a cell with i "effective receptors", and D is the total effect of a ligand on the target cell population.

Importantly, if a ligand interacts with several target cell populations then several effector functions will be constructed for each population depending on its individual PK/PD features.

The time course of the EF(s) during the whole period of ligand-induced effect on the target cell population(s) constitutes an output of the PD module and an input of the TO module.

3. TO Module Description

TO module is designed to propose the most promising schedules of treatment of a specific disease by a specific ligand in a specific patient and/or patient population. In each case of ligand-disease-patient a qualified specialist (such as a physician, a pharmacist, a scientist, a drug developer, etc.) provides specific criteria of treatment optimality to be taken into account (such as minimal target cell population at the end of the treatment, minimal total administered ligand amount, etc.). These criteria are incorporated in TO module in the form of a fitness function, which attributes a certain value to each possible time course of the EF. Next a space of all possible drug administration schedules is searched in order to find a schedule with a maximal fitness function value. Depending on the specific case this search can be performed either by analytical methods or by numerical methods of Operation Research Theory.

Determination of the Model Parameters

In order to implement the invention for realistic analysis of a specific case substitution of specific values of all parameters in PK and PD modules must be done (such as PK of the ligand in blood, production of the receptor by target cells, etc).

The model may be fit to average population or individual patients or patient subpopulations with diverse sets of relevant parameters. To obtain an ideal fitness of the model to each patient/patient population, the patient-related parameters should be given individually for each case.

Some of parameters can be directly measured in each general/individual case. However, sometimes the only available patient-related data are the graphic representation of the time course of a certain model variable (e.g., ligand concentration in the blood). In these cases the model parameters are found by the methods of Operation Research Theory until a good compliance of the model graphic output and the patient's graphs is achieved (similarly to the determination of the optimal treatment protocol—see below).

An Exemplary Implementation

An exemplary implementation is described herein wherein a monoclonal antibody (a ligand), which binds to a specific antigen (a receptor) on the cancerous target cell population, and thereby destroys it.

While further, for clarification of the disclosed teachings, the specific case of monoclonal antibodies is described. It should be emphasized that the disclosed techniques can be applied to any soluble molecular drug, whose intended use or side effect is induced through specific interaction with cell-surface molecules on a certain target cell population.

The following general assumptions are made for the analysis of this specific example:

The antigen production is of zero order kinetics (a constant). It can vary between different cell populations.

One monoclonal antibody molecule is assumed to react with one antigen molecule.

Both free and bound antigens undergo internalization with a first order kinetics. The rates of internalization can differ between bound and free antigens.

Since the blood PK of MAs is much slower than the kinetics of its binding and internalization, it can be assumed that there is a constant (zero order) inflow of MAs into the area of a tumor adjacent to the blood vessels. The further analysis is restricted to the dynamics in this tumor area.

MAs undergo a non-specific first order elimination in the area of the interest (such mechanisms as the extracellular fluid convection, clearance by the reticuloendothelial system, etc.).

The rates of a cell division and of a cell death are much slower than the analyzed dynamics of monoclonal antibody binding. Therefore the cell number is considered to be a constant.

The resultant biological system can be described by the following system of coupled ordinary differential equations:

$$\frac{dA}{dt} = -k_b \cdot A \cdot R + k_u \cdot B + A_0 - \alpha \cdot A, \quad (1)$$

$$\frac{dR}{dt} = -k_b \cdot A \cdot R + k_u \cdot B + P - k_e \cdot R, \quad (2)$$

$$\frac{dB}{dt} = k_b \cdot A \cdot R - k_u \cdot B - k_i \cdot B, \quad (3)$$

where $A(t)$, $R(t)$ and $B(t)$ stand for the molar concentrations (as functions of time) in the extracellular fluid of the free antibodies, of the free antigens and of the bound antigens correspondingly. Here $k_b$ stands for the reaction rate of binding of free antigens, $A_0$ stands for the inflow rate of free antibodies from the blood into the extracellular fluid, P is the production rate of free antigens, and finally, $k_u$, $k_e$, $k_i$ and $\alpha$ are rates of the bound antigen dissociation, of the free antigen internalization, of the bound antigen internalization and of the free antibody elimination correspondingly.

In the case of conjugated antibodies, the following differential equation is provided as well:

$$\frac{dS}{dt} = k_i \cdot B - k_d \cdot S, \quad (4)$$

where $S(t)$ stands for the intracellular concentration (as a function of time) of an internalized conjugate and $k_d$ stands for the rate of its elimination (other constants were defined above).

It can be shown that the system of differential equations (1), (2), (3) has unique positive steady state solution, $A_s$, $R_s$, $B_s$, which is at least locally stable.

The behavior of an individual cell and its interaction with a monoclonal antibody is described herein. It is assumed that concentration of monoclonal antibodies has achieved its steady state value, and all cells in a studied domain are exposed to the same monoclonal antibody concentration.

Consider the following model of an individual cell interaction with monoclonal antibodies. There are two kinds of antigens on the cell surface: free ones and bound ones. One of 5 following possible events can happen with a cell that has i bound antigens and j free ones, during a small time $\Delta t$:
- one of free antigens binds a monoclonal antibody with the probability $k_b A_s j \Delta t + o(\Delta t)$;
- one of free antigens undergoes internalization with the probability $k_e j \Delta t + o(\Delta t)$;
- one of bound antigens undergoes internalization with the probability $k_i i \Delta t + o(\Delta t)$;
- one of bound antigens dissociates with the probability $k_u i \Delta t + o(\Delta t)$;
- a new free antigen is produced with the probability $P \Delta t + o(\Delta t)$;

where the coefficients are the same as in the system of the equations (1), (2) and (3). $A_s$ stands for a steady state concentration of the free antibodies.

Following these definitions, the interaction of monoclonal antibody molecules with a population of cells bearing the corresponding antigen can be described as a countable Markov chain continuous in time.

It can be shown that the limit at infinite time of the distribution of the probabilities of a cell to have i bound antigens and j free ones is equal to $$V_{i,j} = \frac{(k_b A_s)^i \cdot (k_i + k_u)^j \cdot P^{i+j}}{(k_b A_s k_i + k_e k_i + k_e k_u)^{i+j} \cdot i! \cdot j! \cdot \exp\left(\frac{(k_b A_s + k_i + k_u)P}{k_b A_s k_i + k_e k_i + k_e k_u}\right)}. \quad (5)$$

Summation over j of $V_{i,j}$ yields the distribution of the probabilities of a cell to have i bound antigens:

$$W_i = \sum_{j=0}^{\infty} V_{i,j} = \frac{\left(\frac{k_b A_s P}{k_b A_s k_i + k_e k_i + k_e k_u}\right)^i}{i! \cdot \exp\left(\frac{k_b A_s P}{k_b A_s k_i + k_e k_i + k_e k_u}\right)}. \quad (6)$$

As has been indicated previously, PD describes the actual effects of bound and/or internalized ligands on the target cells.

Again, consider as an example a system of monoclonal antibodies and a target cancer cell population. Monoclonal antibodies can be cytotoxic to the target cells by the following mechanisms:
- A complement-dependent cytotoxicity—acomplement activation is induced by the Fc part of the antibody, which leads to perforation of the cellular membrane and to a cell death.
- A cell-mediated cytotoxicity—Fc part of the antibody activates NK cells or macrophages through Fc-receptors, and they induce target cell death.
- A monoclonal antibody is conjugated to a toxin or to a chemotherapeutic agent, which causes the cell damage upon internalization.
- A monoclonal antibody is conjugated to a radionuclide. It is expected that the monoclonal antibody will increase the concentration and will prolong the half-life of the radionuclide in the tumor tissue, resulting in the cell damage.

In first two cases, the cytotoxicity depends on the amount of membrane-bound antibodies, which can be calculated according to the equation (6). In the third case, the intracellular concentration of the toxic conjugates is a variable to be considered in the PD model. It can be calculated according to the equation (4). In the fourth case, the total amount of radionuclides per cell should be calculated as the sum of bound and internalized monoclonal antibody pools. For the first two cases, the function B(i) (the value of EF in a cell with i "effective receptors") can be introduced so that it describes the dependence of the cytotoxicity on the number of bound antigens i. Accordingly, the fraction of damaged/killed cells D can be calculated:

$$D = \sum_{i=0}^{\infty} W_i B(i). \quad (7)$$

In order to be able to assess the effectiveness of a specific monoclonal antibody drug (i.e. the cytotoxicity of the drug) one needs to understand whether its effect depends on the amount of antibodies bound to cell's membrane, on the amount of internalization or both. Using the disclosed techniques one can compute the above amounts using equations (6) and (4). The total effect of the monoclonal antibody on the target cancer cells, i.e. the amount of killed cells, can be computed using equation (7). Equation (7) may be used once an effector function B is formed such that B(i) denotes the monoclonal antibody effect on a cell with i bound/internalized antibodies.

An Example of Practical Implementation of the Invention

In this example, the drug-induced thrombocytopenia as a side effect of a drug, which is a monoclonal antibody is studied. A previously published model of the thrombopoiesis (Skomorovski et al.) together with the currently described model is applied to the experimental data (platelet counts following the drug administration in monkeys). The model PK and PD parameters were adjusted according to the data. FIG. 1 shows the comparison of the model predictions with the actual experimental data in four different monkeys.

The subsequent analysis of the data by our model allowed to pinpoint the most probable mechanism of the drug-induced thrombocytopenia out of several possibilities (the damage to circulating platelets or to bone marrow platelet precursors or both; non-specific damage versus the antibody-mediated specific cytotoxicity), and to determine the parameters that govern the individual susceptibility to the drug-induced thrombocytopenia in different species and ages of the studied monkeys.

In the above example, the effort was to understand the Pharmacodynamics (PK), Pharmacokinetics (PD) and the drug toxicity mechanism of a drug. The drug under study is a monoclonal antibody. The mathematical equations of the model which served for calculating the PK, PD parameters of the drug are described. These parameters govern the susceptibility to the drug induced thrombocytopenia in different species and ages of monkeys.

The ITP-like drug-action mechanism is described. This mechanism, among all drug-action mechanisms tested in our work, proved to have the highest probability of describing the drug's action mechanism. In addition to determining the most probable drug-action mechanism, it was also found that the peripheral blood compartment is the primary target cell population. Thus, for simplicity of explanation, we refer only to the peripheral blood. However, the mathematical model described below was applied to other thrombopoietic compartments as well.

It is important to realize that the equations below focus only on clearance of platelets from the peripheral blood as a result of the drug's action. These equations make only a part—the drug pharmacodynamics link in a very complex chain of dozens of equations, describing the thrombopoietic process, starting from stem cells and moving through all bone marrow phases, up to the platelets in the peripheral blood (For details, see U.S. patent application Ser. No. 09/827,229, which is incorporated herein by reference). Some of these equations refer to platelets turnover (kinetics) in the peripheral blood independent of the drug.

General Assumptions

The thrombopoiesis simulation is a system of discrete-time difference equations. These equations calculate the state of the thrombopoietic lineage in a certain time, according to the state of the system at the previous moment. One, however, should distinguish between two types of time scale: a (slow) biological time scale and a (fast) chemical one.

The biological time step is a basic single iteration of the simulation. In each iteration, necessary update of all the variables of the thrombopoietic system takes place. Among these variables it can be found for example, the maturation of cells in different compartments; update of platelet count, update of the thrombopoietin (TPO) level, creation of new platelets and evolution of the age distribution of platelets and of BM cells at the different compartments.

The chemical time step is the process whereby drug (or any other exogenous chemical substance for that matter) actually takes its action. For example, this is the time when the drug may bind epitopes on platelet (or cells) membrane and hence induce their elimination by reticuloendothelial system (RES). During this step, we compute the distribution of the drug-bound epitopes on platelets as a function of drug's level in the peripheral blood.

It is also assumed that the chemical time scale is much shorter than the biological time scale, so that the number of platelets can be assumed to remain unchanged during the chemical time-step.

ITP-like Drug-action Mechanism

It is assumed that the binding of the drug molecules (or complexes; hereafter both possibility will be denoted as "the drug") to the platelets (cells), which induce platelet elimination through recognition of the platelet by RES. It is assumed that the probability for a platelet to be "captured" by RES is a function of the number of hypothetical drug binding sites, or epitopes, on the platelet's surface and that there are:

m—epitopes on each platelet.

The elimination rate of platelets by RES is defined:

$$F(i) = A \frac{i^n}{i^n + b^n}, \text{ where}$$

i—number of its drug-bound epitopes on a single platelet,
A—maximal RES elimination ability,
b—number of drug-bound epitopes for the elimination to occur at 50% of the maximal rate and
n—steepness coefficient.

For an easier implication of the model in a simulation tool, we created a new parameter
$i_0$—number of drug-bound epitopes for the elimination to occur at 90% of the maximal rate. The one-to-one relation between $i_0$ and n is $i_0 = \sqrt[n]{9} \cdot b$.

The following represents a chemical-equation of binding of the drug to the epitopes:

$$x + p \leftrightarrow c$$

with rate constants $k_1$ (association) and $k_2$ (dissociation) where:
x—concentration of the drug at a given time in peripheral blood,
p—concentration of free epitopes in peripheral blood and
c—concentration of the drug-bound epitopes in peripheral blood.

In terms of dynamics this chemical equation is described by a system of two ordinary differential equations:

$$\frac{dc}{dt} = k_1 x p - k_2 c$$

$$\frac{dp}{dt} = \frac{dx}{dt} = k_2 c - k_1 x p$$

If N is the—number of platelets, then note that:

$$c + p = m \cdot N.$$

As previously described it is assumed that the chemical time scale of the drug binding and dissociation is much shorter than the biological time scale of platelet dynamics. Consequently, N is constant during the chemical step. It is well known that the above system converges to a quasi steady-state satisfying the following:

$$x_s = \frac{1}{2} \left( x - p - Kd + \sqrt{Kd^2 + 2Kd(x+p) + (x-p)^2 + 4Kd \cdot c} \right),$$

where
$x_s$—concentration of the drug in peripheral blood at the quasi steady state.

For obtaining the number of platelets to be eliminated at each biological time step, the distribution of the number of platelets with i drug-bound epitopes is calculated (so as to apply to each of these values the elimination probability dictated by F(i)). In order to compute the histogram denoted V, what happens between the platelets and the epitopes is represented as a Markov process; in other words, vectors $[N_0, N_1, \ldots, N_m]$ are considered where $N_i$—number of platelets with i drug-bound epitopes, and use Markov's theorem to establish that the iterations of the process converge to the fixed vector $$\tilde{V}_i = \frac{\binom{m}{i} \left(\frac{x_s}{Kd}\right)^i N}{\left(1 + \frac{x_s}{Kd}\right)^m}, \quad 0 \leq i \leq m.$$

Here, $$Kd = \frac{k_2}{k_1}$$

is the dissociation constant.
The amount of platelets to be eliminated by RES is:

$$V = \sum_{i=0}^{m} \tilde{V}_i F(i).$$

This sum is introduced as a part of the differential equation describing general platelets dynamics altogether, with the "normal" thrombopoiesis model (i.e., without the presence of the drug).

As easily can be seen, the actual drug-induced thrombocytopenia depends on three groups of factors:

1. Thrombopoiesis parameters (not included in this document).
2. Factors determining the drug-Platelet interaction: two unknown parameters (m and Kd) and two known variables (the drug's concentration and platelet count).
3. Factors determining RES ability to eliminate the drug-bound platelets: three unknown parameters (A, b and $i_o$).

Results—Synopsis

1. Average parametric results as estimated by the above technique technology for comparison between age groups.

| Adults (Cynomolgus) | | | | |
|---|---|---|---|---|
| Number of animals | | 11 | | |
| Average age (months) | | 49.81 | | |
| Parameter | Average | S.D. | C.V. | Search range |
| Kd (nM) | 12,137 | 7,224 | 0.5952 | 220-22,000 |
| b | 20.112 | 12.388 | 0.616 | 5-50 |
| $i_o$ | 115.18 | 53.135 | 0.4613 | 8.66-216.33 |
|  | 0.566 | 0.269 | 0.4763 | 0.05-0.95 |
| m | 206.57 | 45.4 | 0.22 | 10-250 |

| Juveniles (Cynomolgus) | | | | |
|---|---|---|---|---|
| Number of animals | | 9 | | |
| Average age (months) | | 8.88 | | |
| Parameter | Average | S.D. | C.V. | Search range |
| Kd (nM) | 3,599 | 4,149 | 1.153 | 220-22,000 |
| b | 14.875 | 9.405 | 0.6322 | 5-50 |
| $i_o$ | 120.2 | 72.423 | 0.6025 | 8.66-216.33 |
|  | 0.734 | 0.254 | 0.3466 | 0.05-0.95 |
| m | 223.1 | 31.47 | 0.141 | 10-250 |

2. Average parametric results for comparison between species groups:

| AGM (Adults) | | | | |
|---|---|---|---|---|
| Number of animals | | 6 | | |
| Average age (months) | | 182 | | |
| Parameter | Average | S.D. | C.V. | Search range |
| Kd (nM) | 12,683 | 4,222 | 0.333 | 220-22,000 |
| b | 28.65 | 14.156 | 0.494 | 5-50 |
| $i_o$ | 113.133 | 55.139 | 0.4874 | 8.66-216.33 |
|  | 0.469 | 0.2744 | 0.5852 | 0.05-0.95 |
| m | 175.266 | 59.935 | 0.342 | 10-250 |

| Cynomolgus (Adults) | | | | |
|---|---|---|---|---|
| Number of animals | | 5 | | |
| Average age (months) | | 112.8 | | |
| Parameter | Average | S.D. | C.V. | Search range |
| Kd (nM) | 6,515 | 5,092 | 0.7816 | 220-22,000 |
| b | 14.312 | 9.171 | 0.641 | 5-50 |
| $i_o$ | 101.715 | 65.98 | 0.6487 | 8.66-216.33 |
|  | 0.625 | 0.1511 | 0.242 | 0.05-0.95 |
| m | 185.836 | 58.548 | 0.315 | 10-250 |

| Rhesus (Adults) | | | | |
|---|---|---|---|---|
| Number of animals | | 5 | | |
| Average age (months) | | 304.8 | | |
| Parameter | Average | S.D. | C.V. | Search range |
| Kd (nM) | 14,057 | 6,993 | 0.4975 | 220-22,000 |
| b | 29.015 | 12.433 | 0.4285 | 5-50 |
| $i_o$ | 93.998 | 53.98 | 0.5743 | 8.66-216.33 |
|  | 0.3839 | 0.251 | 0.6523 | 0.05-0.95 |
| m | 165.24 | 58.026 | 0.3512 | 10-250 |

| Chimps (Adults) | | | | |
|---|---|---|---|---|
| Number of animals | | 6 | | |
| Average age (months) | | 132 | | |
| Parameter | Average | S.D. | C.V. | Search range |
| Kd (nM) | 11,611 | 7,149 | 0.6157 | 220-22,000 |
| b | 20.555 | 11.116 | 0.5408 | 5-50 |
| $i_o$ | 142.266 | 59.286 | 0.4167 | 8.66-216.33 |
|  | 0.5015 | 0.229 | 0.4568 | 0.05-0.95 |
| m | 191.6 | 57.907 | 0.3022 | 10-250 |

Illustrative Applications of the Disclosed Techniques

The presented method of analysis of ligand-target cell interactions allows the calculation of the expected ligand efficacy in vivo based solely on parameters, which can be evaluated experimentally in vitro by existing well-established techniques, including a radioimmunoassays and a FACS (a fluorescence-assisted cell sorting).

The following examples of clinical applications of the model are proposed:

During an early drug development stage: given a target cell population to choose the most promising receptor candidates, to which a specific ligand will be synthesized, as well as the most promising type of a ligand (a small peptide, an unconjugated MA, a MA-toxin conjugate, etc).

During the pre-clinical evaluation of a drug: given a target cell population and a ligand to choose the optimal schedule of its administration, while the criteria for optimality can include the minimal amount of the ligand, the minimal toxicity, the maximal efficacy, etc.

An individualization of a treatment: given individual parameters of a target cell population in a specific patient to choose the most suitable targeted molecular therapy (both the drug(s) and their administration schedule).

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A computer system for recommending an optimal treatment protocol for a human patient comprising:
   a model of biological processes related to a disease for the human patient;
   a treatment protocol generator for generating a plurality of treatment protocols for treating the disease in the human patient using drugs;
   a treatment protocol generator that creates treatment protocol space;

a selector adapted to select an optimal treatment protocol from said plurality of treatment protocols generated from the treatment protocol generator based on the model, and a computer processor;

the model, further comprising:

a pharmacokinetics macro module adapted to analyze interactions between a ligand and a population of target cells at a tissue level in the human patient;

a pharmacokinetics micro module adapted to analyze interactions between the ligand and a cell at an individual cell level in the human patient;

the micro module adapted to model behavior of the ligand and receptors related to single cell level of ligand-cell interactions, as a stochastic process;

wherein the computer system outputs a recommendation for the optimal treatment protocol for the human patient to a user; and wherein the number of receptors is not constant.

2. The system of claim 1 wherein the model further comprises a pharmacodynamics module that is adapted to model actual effects of ligands on the population of target cells using pharmacokinetics modules' outcome.

3. The system of claim 2, wherein the pharmacokinetics micro module is operable to compute a distribution of cells according to a number of bound receptors and a number of free receptors in a cell.

4. The system of claim 3, wherein the distribution of cells is provided to the pharmacodynamics module.

5. The system of claim 1, wherein the stochastic process is a Markov chain.

6. The system of claim 1, wherein the ligand is a monoclonal antibody.

7. The system of claim 1, wherein the receptors are antigens on cell surface of said target cells.

8. The system of claim 1, wherein the target cell population is cancerous.

9. The system of claim 1, wherein, the pharmacokinetics macro module is a system of differential equations, each of said differential equations describing behavior of a separate parameter.

10. The system of claim 5, wherein the Markov chain is countable and continuous in time.

11. The system of claim 9, wherein the differential equations include at least one selected from an equation denoting molar concentrations of free antibodies as a function of time, equation denoting molar concentrations of free antigens as a function of time, equation denoting molar concentrations of bound antigens as a function of time, equation denoting molar concentrations of internalized conjugates.

12. The system of claim 10, wherein a base set of the Markov chain is chosen to form an infinite grid of states wherein each of said states is a cell that includes a set of free antigens and a set of bound antigens.

13. The system of claim 12, wherein the model is adapted to consider at least one of next moves selected from: a free antigen binding with an antibody; a free antigen undergoing internalizations, a bound antigen undergoing internalization, a bound antigen disassociating and a new free antigen being produced, wherein each of the next moves proceeds with a predetermined probability density.

14. The system of claim 1, wherein the pharmacokinetics macro module is assumed to arrive at steady state prior to implementing the micro module.

15. The system of claim 2, wherein the pharmacodynamics module includes an effector function that computes ligand effects.

16. The system of claim 1 further comprising:

a model modifier operable to modify the model based on parameters specific to an individual.

17. A computer-implemented method for recommending an optimal treatment protocol for treating a disease in a human patient comprising:

obtaining data from a patient to create a model for biological processes related to the disease for the human patient;

modeling biological processes related to the disease for the human patient using the model;

creating treatment protocol space for treating the disease in the human patient using drugs, with a treatment protocol generator;

selecting an optimal treatment protocol for the human patient from said plurality of treatment protocols enumerated from the treatment protocol generator, based on the modeling;

recommending said optimal treatment using a computer processor; and outputting recommendation for said optimal treatment for the human patient to a user;

wherein the step of modeling further includes:

analyzing interactions between a ligand and a population of target cells at a tissue level in the human patient using a pharmacokinetics macro module;

analyzing interactions between the ligand and a cell at an individual cell level in the human patient using a pharmacokinetics micro module;

wherein the pharmacokinetics micro module models behavior of the ligand and receptors related to single cell level of ligand-cell interactions, as a stochastic process;

wherein the number of receptors is not constant.

18. The computer-implemented method of claim 17 further comprising:

modeling actual effects of ligands on the population of target cells using pharmacokinetics modules' outcome using a pharmacodynamics module.

19. The computer-implemented method of claim 18, further comprising:

computing a distribution of cells according to a number of bound receptors and a number of free receptors in a cell using the pharmacokinetics micro module.

20. The computer-implemented method of claim 19, further comprising:

providing the distribution of cells to the pharmacodynamics module.

21. The computer-implemented method of claim 17, wherein the stochastic process is a Markov chain.

22. The computer-implemented method of claim 17, wherein the ligand is a monoclonal antibody.

23. The computer-implemented method of claim 17, wherein the receptors are antigen on cell surface of said target cells.

24. The computer-implemented method of claim 17, wherein the target cell population is cancerous.

25. The computer-implemented method of claim 17, wherein, the pharmacokinetics macro module is a system of differential equations, each of said differential equations describing behavior of a separate parameter.

26. The computer-implemented method of claim 21, wherein the Markov chain is countable and continuous in time.

27. The computer-implemented method of claim 25, wherein the differential equations include at least one selected from an equation denoting molar concentrations of free antibodies as a function of time, equation denoting molar concentrations of free antigens as a function of time, equation denoting molar concentrations of bound antigens as a function of time, equation denoting molar concentrations of internalized conjugates.

28. The computer-implemented method of claim 26, wherein a base set of the Markov chain is chosen to form an infinite grid of states wherein each of said states is a cell that includes a set of free antigens and a set of bound antigens.

29. The computer-implemented method of claim 28, wherein the model is adapted to consider at least one of next moves selected from: a free antigen binding with an antibody; a free antigen undergoing internalizations, a bound antigen undergoing internalization, a bound antigen disassociating and a new free antigen being produced, wherein each of the next moves proceeds with a predetermined probability density.

30. The computer-implemented method of claim 17, wherein the pharmacokinetics macro module is assumed to arrive at steady state prior to implementing the micro module.

31. The computer-implemented method of claim 18, wherein the pharmacodynamics module includes an effector function that computes ligand effects.

32. The computer-implemented method of claim 17 further comprising:

modifying the model based on parameters specific to an individual.

\* \* \* \* \*